US008852125B2

(12) United States Patent
Von Malmborg

(10) Patent No.: US 8,852,125 B2
(45) Date of Patent: Oct. 7, 2014

(54) MALE CONNECTOR

(75) Inventor: Pär Von Malmborg, Uppsala (SE)

(73) Assignee: St. Jude Medical Systems AB, Uppsala (SE)

( * ) Notice: Subject to any disclaimer, the term of this patent is extended or adjusted under 35 U.S.C. 154(b) by 793 days.

(21) Appl. No.: 12/739,064

(22) PCT Filed: Oct. 27, 2008

(86) PCT No.: PCT/SE2008/051215
§ 371 (c)(1),
(2), (4) Date: Apr. 21, 2010

(87) PCT Pub. No.: WO2009/054805
PCT Pub. Date: Apr. 30, 2009

(65) Prior Publication Data
US 2010/0262040 A1     Oct. 14, 2010

Related U.S. Application Data

(60) Provisional application No. 60/996,071, filed on Oct. 26, 2007.

(51) Int. Cl.
*A61B 5/00*         (2006.01)
*A61M 25/00*        (2006.01)
*A61B 5/0215*       (2006.01)
*A61M 25/09*        (2006.01)

(52) U.S. Cl.
CPC .......... *A61M 25/09* (2013.01); *A61B 2562/227* (2013.01); *A61B 5/0215* (2013.01); *A61B 5/6851* (2013.01)
USPC .......................................... 600/585; 604/523

(58) Field of Classification Search
CPC ........... A61B 2562/227; A61B 5/0215; A61B 5/6851; A61M 25/09
USPC ..................... 600/585; 604/523; 29/831, 854
See application file for complete search history.

(56) References Cited

U.S. PATENT DOCUMENTS

| 5,163,445 A | 11/1992 | Christian et al. |
| 6,090,052 A | 7/2000 | Akerfeldt et al. |
| 6,196,980 B1 | 3/2001 | Akerfeldt et al. |

(Continued)

FOREIGN PATENT DOCUMENTS

DE            4104215 A1 *  8/1992

OTHER PUBLICATIONS

English Abstract of DE 4104215 A1.*

*Primary Examiner* — Adam Eiseman
(74) *Attorney, Agent, or Firm* — Foley & Lardner LLP

(57) ABSTRACT

A male connector for a sensor guide wire for intravascular measurements of physiological variables in a living body, and a method for producing said male connector. The male connector comprises a plurality of spaced apart conductive members, extending at least partially along the length of the male connector, and a plurality of conductive areas separated from each other by insulating areas, disposed along the male connector, wherein each of the conductive members are connected to a respective conductive area. The conductive members and the conductive and insulating areas are formed on a planar sheet of thin flexible insulating material, and the conductive members are provided on one surface of the sheet and the conductive areas are provided on the other surface of the sheet, wherein said planar sheet is adapted to be formed into said male connector such that said conductive member being arranged at the inner surface, and that said conductive and insulating areas being arranged at the outer surface of the male connector.

13 Claims, 4 Drawing Sheets

(56) References Cited

U.S. PATENT DOCUMENTS

| | | |
|---|---|---|
| 6,779,257 B2 * | 8/2004 | Kiepen et al. .................. 29/825 |
| 6,908,442 B2 | 6/2005 | Von Malmborg et al. |
| 7,676,910 B2 * | 3/2010 | Kiepen et al. .................. 29/825 |
| 8,332,052 B1 * | 12/2012 | Orinski ........................ 607/137 |
| 2005/0091833 A1 | 5/2005 | Kiepen et al. |
| 2008/0247747 A1 * | 10/2008 | Darbha et al. ................ 396/428 |

* cited by examiner

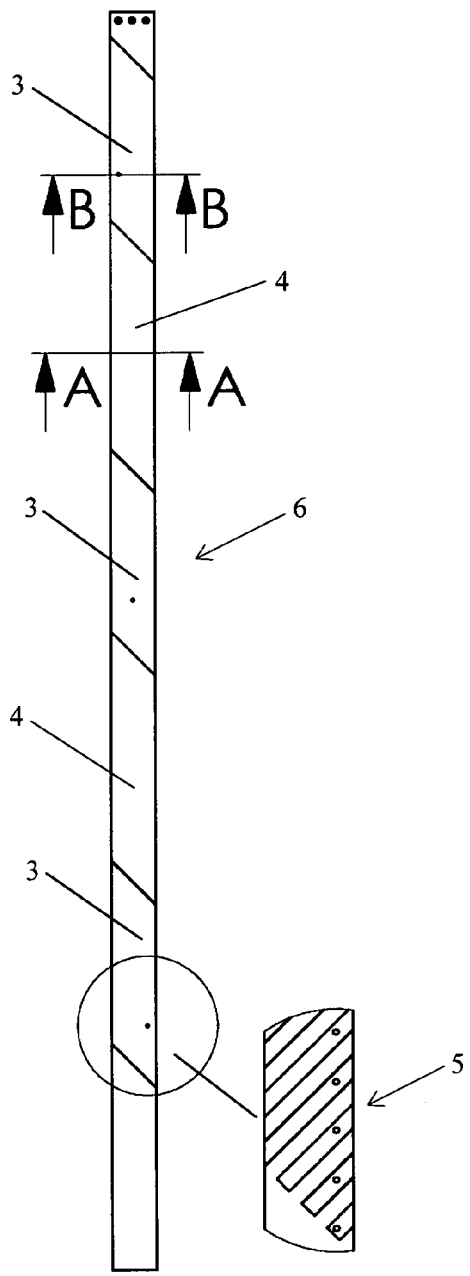
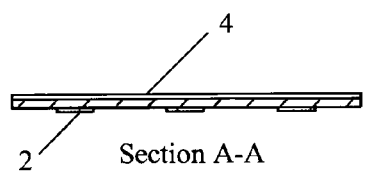
Section A-A
FIG. 2
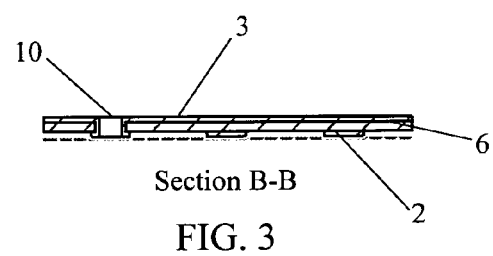
Section B-B
FIG. 3
FIG. 1

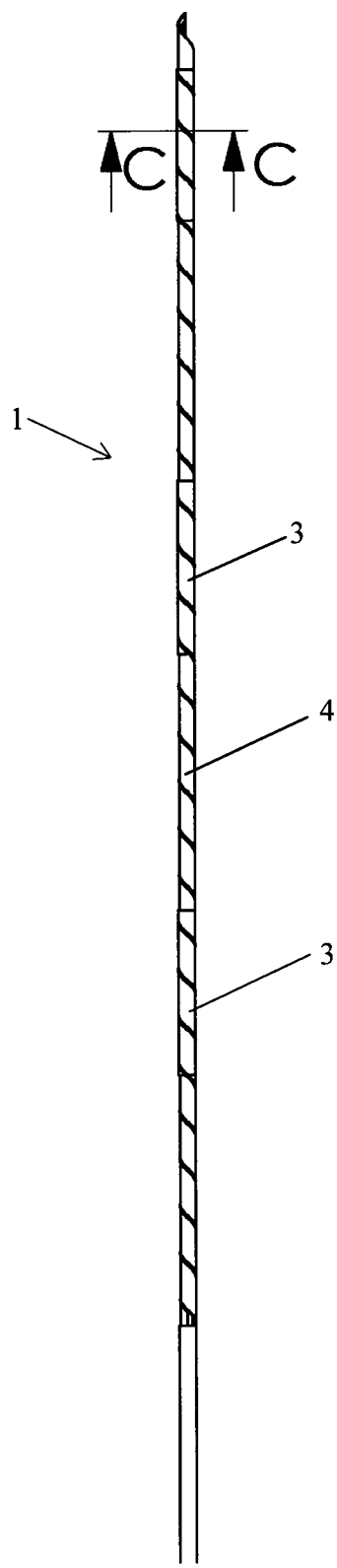
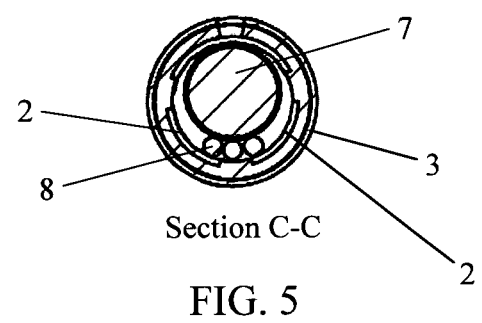
Section C-C
FIG. 5
FIG. 4

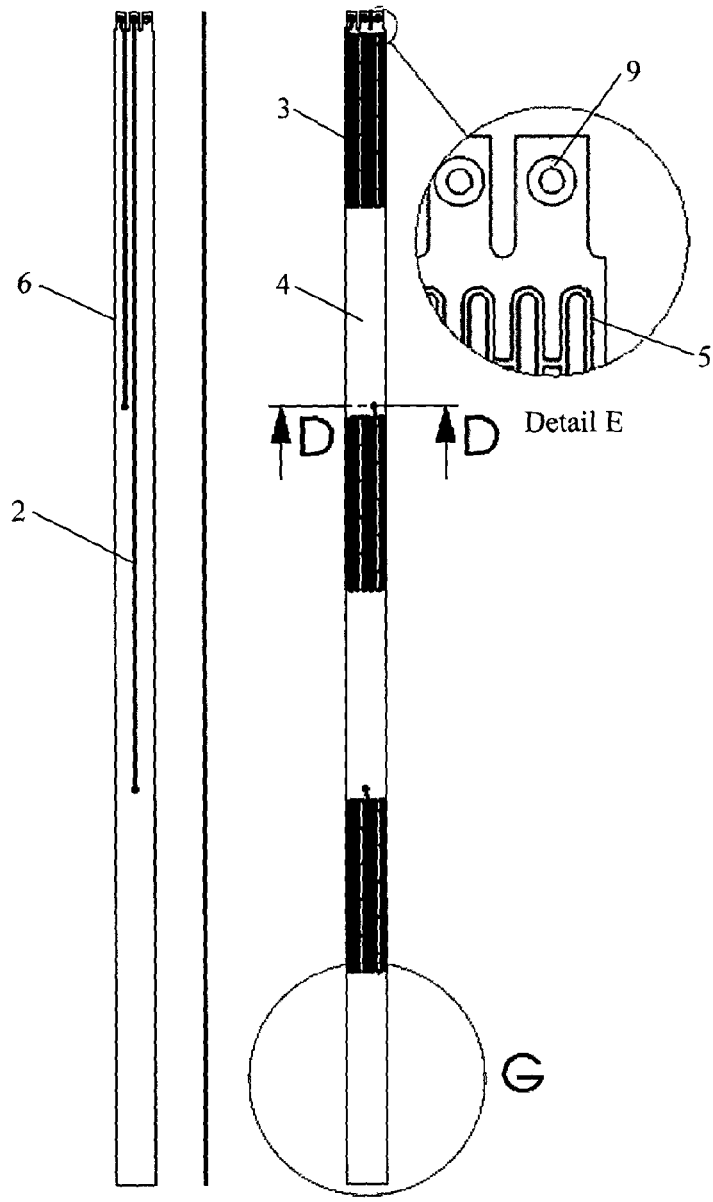
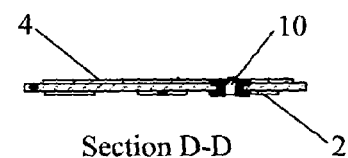
Section D-D
FIG. 7
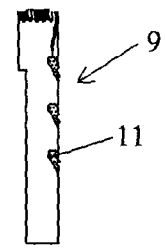
Detail G
FIG. 8
FIG. 6a    FIG. 6b

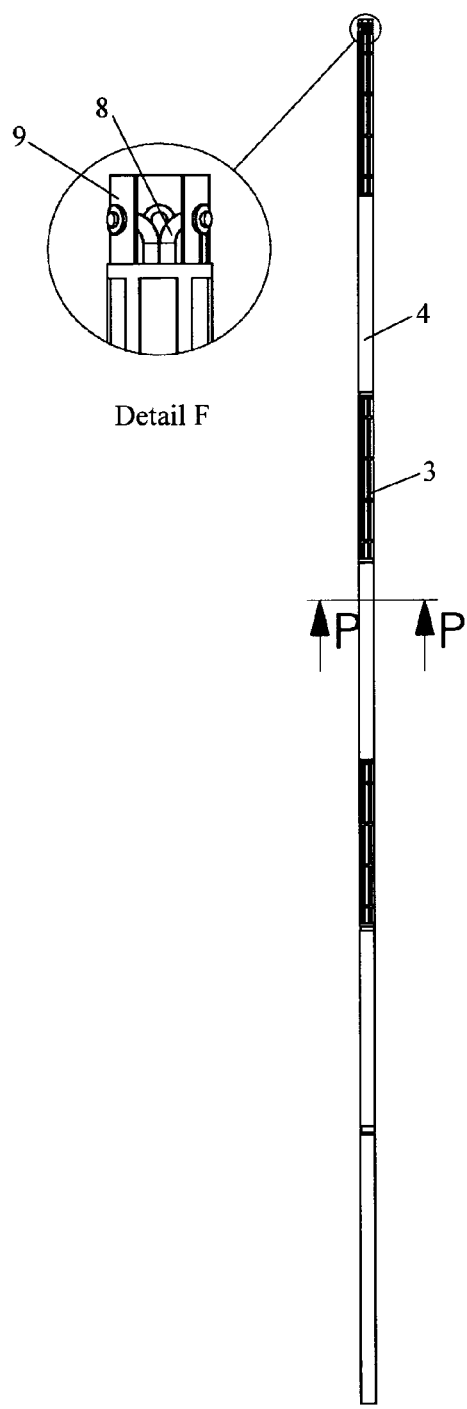
Detail F
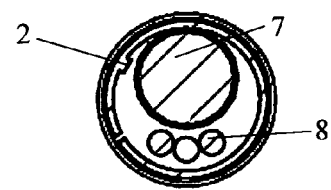
Section P-P
FIG. 10
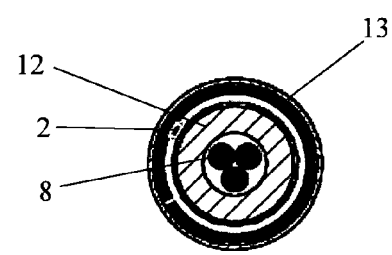
Section P-P
FIG. 11
FIG. 9

MALE CONNECTOR

FIELD OF THE INVENTION

The present invention relates to a male connector, and also to a method for producing said male connector, for a sensor guide wire for intravascular measurements of physiological variables in a living body according to the preambles of the independent claims.

BACKGROUND OF THE INVENTION

In many medical procedures, various physiological conditions present within a body cavity need to be monitored. These physiological conditions are typically physical in nature—such as pressure, temperature, rate-of-fluid flow, and provide the physician or medical technician with critical information as to the status of a patient's condition.

One device that is widely used to monitor conditions is the blood pressure sensor. A blood pressure sensor senses the magnitude of a patient's blood pressure, and converts it into a representative electrical signal that is transmitted to the exterior of the patient. For most applications it is also required that the sensor is electrically energized.

Some means of signal and energy transmission is thus required, and most commonly extremely thin electrical cables are provided inside a guide wire, which itself preferably is provided in the form of a tube, which often has an outer diameter in the order of 0.35 mm, and oftentimes is made of steel. In order to increase the bending strength of the tubular guide wire, a core wire is positioned inside the tube. The mentioned electrical leads are positioned in the space between the inner lumen wall and the core wire.

In a guide wire mounted sensor, the signals from the sensor, arranged at the distal end of the guide wire, are lead through the electrical leads to a male connector at the proximal end of the guide wire. In use, the male connector is connected to a corresponding female connector and the signals from the pressure sensor are transferred to an interface, which converts the signals and presents them in a desired form for an operator.

A conventional male connector basically comprises a core wire, a plurality of conductors, a plurality of conductive members, and insulating material therebetween. When the male connector is connected to the female connector, the conductive members transfer the signals from the conductors of the male connector to similar conductive members inside the female connector. Several different designs of such male connectors are known in the prior art, and examples of such male connectors are disclosed in U.S. Pat. No. 6,196,980 B1, and U.S. Pat. No. 6,908,442 B2, which both are assigned to the same assignee as in the present application.

In U.S. Pat. No. 6,090,052 A, also assigned to the same assignee as in the present application, a male connector comprising a sheet of thin flexible material, on which the electrical leads are provided, is disclosed. The sheet has the general shape of the letter L, or a flagstaff with a hoisted flag.

The manufacturing of such thin flexible sheet for male connectors and the mounting of the thin flexible sheets on the male connector are time-consuming and thus an expensive procedure, and the object of the present invention is to achieve an improved male connector that is easier to manufacture and assemble than presently used male connectors which render the overall manufacturing cost less expensive.

SUMMARY OF THE INVENTION

Thus, the object of the present invention is achieved by a male connector for a sensor guide wire for intravascular measurements of physiological variables in a living body, in accordance to the present invention. The male connector comprises a plurality of spaced apart conductive members, extending at least partially along the length of the male connector, and a plurality of conductive areas separated from each other by insulating areas, disposed along the male connector, wherein each of the conductive members are connected to a respective conductive area. The conductive members and the conductive and insulating areas are formed on a planar sheet of thin flexible insulating material, and the conductive members are provided on one surface of the sheet and the conductive areas are provided on the other surface of the sheet. The planar sheet is adapted to be formed into the male connector such that the conductive member being arranged at the inner surface, and that the conductive and insulating areas being arranged at the outer surface of the male connector.

The invention will now be described in detail with reference to the drawings.

SHORT DESCRIPTION OF THE APPENDED DRAWINGS

FIG. 1 shows a planar sheet for a male connector according to the present invention.

FIG. 2 shows a cross-section A-A of the sheet shown in FIG. 1.

FIG. 3 shows a cross-section B-B of the sheet shown in FIG. 1.

FIG. 4 shows a sheet which is helically wound to form a male connector.

FIG. 5 shows a cross-section C-C of the male connector shown in FIG. 4.

FIG. 6a shows a surface of the sheet provided with conductive members, and a side view of said sheet.

FIG. 6b shows the other surface of the sheet, provided with conductive and insulating areas, and a detail E of said sheet, which shows cable connectors according to the present invention.

FIG. 7 shows a cross-section D-D of the sheet shown in FIGS. 6a and 6b.

FIG. 8 shows a detail G of the distal end of the sheet in FIG. 6b.

FIG. 9 shows the sheet in FIGS. 6a and 6b, longitudinally folded to form the male connector.

FIG. 10 shows a cross section P-P of the male connector in FIG. 9.

FIG. 11 shows a cross section P-P of the male connector in FIG. 9, according to another embodiment of the present invention.

Throughout the figures the same reference signs designate the same, or essentially the same feature.

DETAILED DESCRIPTION OF PREFERRED EMBODIMENTS OF THE INVENTION

With references to the figures, and initially to FIGS. 1-4, a male connector 1 for a sensor guide wire for intravascular measurements of physiological variables in a living body, according to the present invention, is shown. The male connector 1 comprises a plurality of spaced apart conductive members 2 (shown in FIG. 2), extending at least partially along the length of the male connector 1, and a plurality of conductive areas 3 separated from each other by insulating areas 4, disposed along the male connector 1. Each of the conductive members 2 are connected to a respective conductive area 3, as shown in FIG. 3.

FIG. 1 also shows a detail of a contact surface 5 of a conductive area 3. However, the contact surface 5 can be designed in many different ways.

The conductive members 2 and the conductive and insulating areas 3, 4 are formed on a planar sheet 6 of thin flexible insulating material, as illustrated in FIG. 1. The conductive members 2 are provided on one surface of the sheet and the conductive areas 3 are provided on the other surface of the sheet, as shown in FIGS. 2 and 3. Said planar sheet 6 is adapted to be formed into said male connector 1 such that said conductive member 2 being arranged at the inner surface, and that said conductive and insulating areas 3, 4 being arranged at the outer surface of the male connector 1, as shown in FIGS. 4 and 5.

According to one preferred embodiment of the present invention, as shown in FIG. 4, the sheet 6 is helically wound to form said male connector 1.

FIG. 5 shows a cross-section of the sheet 6 formed into a male connector 1. The male connector 1 is, according to this embodiment, provided with a core wire 7 extending along the length of the male connector 1. The sheet 6 is helically wound around the core wire 7. The conductive members 2 are arranged at the inner surface, and that the conductive and insulating areas 3, 4 are arranged at the outer surface of the male connector 1. The conductive members 2 are adapted to be connected to signal transmitting cables 8 to electrically connect the respective conductive area 3 to a sensor at the distal end of the sensor guide wire. In FIG. 5, the signal transmitting cables 8 extend along the length of and next to the core wire 7 enclosed by the helically wound sheet 6.

FIG. 6a shows an inner surface of the sheet 6 provided with a plurality of spaced apart conductive members 2, extending at least partially along the length of the sheet 6, according to another embodiment of the present invention. FIG. 6a also shows a side view of the planar sheet 6 of thin flexible insulating material.

In FIG. 6b, the outer surface of the sheet 6, provided with a plurality of conductive areas 3 separated from each other by insulating areas 4, is shown. The sheet 6 is an elongated strip. Detail E shows a plurality of cable connectors 9 provided at the proximal end of the sheet 6, which sheet 6 is adapted to be formed into a male connector 1. The cable connectors 9 are used to connect the male connector 1 with at least one signal transmitting cable 8 such that each cable connector is connected to one cable. According to the preferred embodiment shown in detail E, the cable connector 9 is a via hole 10. Detail E also shows an alternative embodiment of the contact surface 5 in the conductive area 3.

The sheet 6 is provided with at least one connection member to electrically connect the conductive member 2 to a conductive area 3. The connection member may be a via hole 10 in the direction perpendicular to the longitudinal direction of the sensor wire, in the area where the conductive member 2 is connected to the conductive area 3, as illustrated in FIG. 3. In FIG. 7, the via hole 10 is arranged in the insulating area 4, however, the via hole 10 is then connected to the conductive area 3 on the outer surface of the sheet 6.

According to one alternative embodiment of the present invention, as illustrated in FIG. 8 (illustrating detail G in FIG. 6b), the sheet 6 is provided with at least one cable connector 9, at the distal end of the male connector 1. The cable connector 9 is, according to this embodiment, a cable connecting groove 11, wherein a signal transmitting cable 8 is adapted to be connected. The cable connector 9 arranged at the distal end is preferably used when the cables 8 are connected after the sheet 6 has been formed into a male connector 1.

FIG. 9 illustrates the sheet 6, longitudinally folded to form the male connector 1. Detail F shows the cable connector 9 provided at the proximal end of the male connector 1. An advantage of arranging the cable connector 9 at the proximal end, in combination with that the male connector 1 is formed by a helically wounded or longitudinally folded sheet 6, is that signal transmitting cables 8 may be connected to the cable connector 9 on the planar sheet 6, shown in FIGS. 1 and 6a-b, and subsequently, after the cables 8 have been connected, the sheet 6 is helically wounded or longitudinally folded around the signal transmitting cables 8 to form said male connector 1.

The sheet 6 may, alternatively, be longitudinally folded around a core wire 7 to form said male connector 1, as illustrated in FIG. 10. The signal transmitting cables 8 are then adapted to be extending along the length of, and next to, the core wire 7, as shown in FIG. 10. The signal transmitting cables 8 may also be adapted to be extending in the centre of a core tube 12, as illustrated in FIG. 11.

The core tube 12 may be a separate core tube 12, extending along the length of the male connector 1, and connected to another core tube extending along the length of the more distal parts of the guide wire, or the core tube 12 may be a continuous core tube 12 extending further along the length of the distal parts of the guide wire. A separate core tube 12, which only extends along the length of the male connector 1, may alternatively be connected to a core wire extending along the length of the distal parts of the guide wire.

According to one preferred embodiment, the core tube 12, extending along the length of the male connector 1, has a smaller diameter than the core tube extending along the length of the more distal parts of the guide wire, in order to achieve equal diameter of the male connector 1 and of the guide wire, after the sheet 6 has been formed around the core tube 12 into said male connector 1.

In the embodiment, wherein the sheet 6 is formed around a core wire 7, shown in FIG. 10, the core wire 7 may in a similar way be a separate core wire 7 or a continuous core wire 7, or the core wire 7 may be connected to a core wire extending along the length of the guide wire. Likewise, the diameter of the core wire 7 extending along the length of the male connector 1 may be smaller than the diameter of the core wire 7 extending along the length of the more distal parts of the guide wire, in order to achieve equal diameters of the male connector 1 and the guide wire.

The sheet 6 is, after being formed into a male connector 1, fixated by a shrink tubing 13 (as shown in FIG. 11), an adhesive, or by welding or soldering.

The present invention also relates to a method for producing a male connector 1, for a sensor guide wire for intravascular measurements of physiological variables in a living body, as illustrated in FIGS. 4 and 9, wherein the method includes the steps of:

a) providing the planar sheet 6 with spaced apart conductive members 2 on one surface, b) providing the planar sheet 6 with conductive areas 2 separated from each other by insulating areas 3 on the other surface, c) connecting each of the conductive members 2 to a respective conductive area 3, d) providing the sheet 6 with at least one connection member to electrically connect the conductive member 2 to a conductive area 3, e) providing the sheet 6 with at least one cable connector 9 adapted to connect the sheet 6 with at least one signal transmitting cable 8, f) forming the sheet (6) into said male connector (1) such that said conductive member (2) is arranged at the inner surface, and that said conductive and insulating areas (3, 4) are arranged at the outer surface of the male connector (1).

According to the method for producing a male connector 1, step e) may further include the sub step of:

e1) connecting at least one signal transmitting cable 8 to the cable connector 9, According to the preferred embodiment shown in FIG. 4, the method for producing a male connector 1 where in step f), the male connector is formed by helically wounding the sheet 6 to form said male connector 1 such that said conductive member 2 is arranged at the inner surface, and that said conductive and insulating areas 3, 4 are arranged at the outer surface of the male connector 1.

Alternatively, according to the preferred embodiment shown in FIG. 9, the method for producing a male connector 1 where in step f), the male connector is formed by longitudinally folding the sheet 6 to form said male connector 1 such that said conductive member 2 is arranged at the inner surface, and that said conductive and insulating areas 3, 4 are arranged at the outer surface of the male connector 1.

The present invention is not limited to the above-described preferred embodiments. Various alternatives, modifications and equivalents may be used. Therefore, the above embodiments should not be taken as limiting the scope of the invention, which is defined by the appending claims.

The invention claimed is:

1. A male connector for a sensor guide wire for intravascular measurement of a physiological variable in a living body, comprising:
   a plurality of spaced apart conductive members, extending at least partially along the length of the male connector, and
   a plurality of conductive areas separated from each other by insulating areas, disposed along the male connector,
   wherein each of the conductive members are connected to a respective conductive area,
   wherein the conductive members and the conductive and insulating areas are formed on an elongated strip of thin flexible insulating material, and the conductive members are provided on a first surface of the elongated strip and the conductive areas are provided on a second, opposing surface of the elongated strip,
   wherein said elongated strip is helically wound to form said male connector such that the conductive members are arranged at an inner surface of the male connector, and the conductive and insulating areas are arranged at an outer surface of the male connector,
   wherein the male connector comprises a plurality of first sections including the conductive areas, and a plurality of second sections including the insulating areas, and
   wherein, in the helically wound state, the first and second sections alternate such that the first sections are insulated from one another by the second sections.

2. A male connector according to claim 1, wherein the conductive members are adapted to be connected to a respective signal transmitting cable to electrically connect the respective conductive areas to a sensor at a distal end of the sensor guide wire.

3. A male connector according to claim 1, wherein the elongated strip is helically wound around a core wire.

4. A male connector according to claim 1, wherein the elongated strip is helically wound around a core tube.

5. A male connector according to claim 1, wherein the elongated strip is provided with at least one connection member to electrically connect a conductive member to a conductive area.

6. A male connector according to claim 5, wherein said connection member is a via hole in a direction perpendicular to a longitudinal direction of the sensor guide wire, in an area where the conductive member is connected to the conductive area.

7. A male connector according to claim 1, wherein the elongated strip is provided with at least one cable connector, at a proximal end of the male connector, adapted to be connected with a signal transmitting cable.

8. A male connector according to claim 7, wherein the cable connector is a via hole.

9. A male connector according to claim 1, wherein the elongated strip is provided with at least one cable connector, at a distal end of the male connector, adapted to be connected to a signal transmitting cable.

10. A male connector according to claim 9, wherein the cable connector is a cable connecting groove.

11. A male connector according to claim 1, wherein the elongated strip is fixated by a shrink tubing, an adhesive, or by welding or soldering.

12. A method for producing a male connector, for a sensor guide wire for intravascular measurement of a physiological variable in a living body, including the steps of:
    providing an elongated strip with spaced apart conductive members on a first surface,
    providing the elongated strip with conductive areas separated from each other by insulating areas on a second surface,
    connecting each of the conductive members to a respective conductive area,
    providing the elongated strip with at least one connection member to electrically connect a conductive member to a conductive area,
    providing the elongated strip with at least one cable connector adapted to connect the elongated strip with at least one signal transmitting cable, and
    forming the elongated strip into said male connector by helically winding the elongated strip such that said conductive members are arranged at an inner surface of the male connector, and such that said conductive and insulating areas are arranged at an outer surface of the male connector,
    wherein the male connector comprises a plurality of first sections including the conductive areas, and a plurality of second sections including the insulating areas, and
    wherein, in the helically wound state, the first and second sections alternate such that the first sections are insulated from one another by the second sections.

13. The method for producing a male connector according to claim 12, wherein the step of forming the elongated strip into said male connector includes connecting at least one signal transmitting cable to the cable connector.

* * * * *